United States Patent
Park et al.

(10) Patent No.: US 10,258,290 B2
(45) Date of Patent: Apr. 16, 2019

(54) METHOD AND APPARATUS FOR PROCESSING BIOSIGNAL

(71) Applicant: Samsung Electronics Co., Ltd., Suwon-si (KR)

(72) Inventors: Chang Soon Park, Chungju-si (KR); Ui Kun Kwon, Hwaseong-si (KR); Sang-joon Kim, Hwaseong-si (KR); Seungkeun Yoon, Seoul (KR); Jaechun Lee, Seoul (KR); Changmok Choi, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 398 days.

(21) Appl. No.: 15/182,956

(22) Filed: Jun. 15, 2016

(65) Prior Publication Data

US 2017/0172514 A1    Jun. 22, 2017

(30) Foreign Application Priority Data

Dec. 18, 2015 (KR) .......................... 10-2015-0181555

(51) Int. Cl.
| | | |
|---|---|---|
| *A61B 5/00* | (2006.01) | |
| *A61B 5/04* | (2006.01) | |
| *G06K 9/00* | (2006.01) | |
| *A61B 5/024* | (2006.01) | |
| *G01R 23/16* | (2006.01) | |
| *A61B 5/0402* | (2006.01) | |
| *A61B 5/0488* | (2006.01) | |

(52) U.S. Cl.
CPC .......... *A61B 5/7257* (2013.01); *A61B 5/0402* (2013.01); *A61B 5/04012* (2013.01); *A61B 5/0488* (2013.01); *A61B 5/7203* (2013.01); *A61B 5/7264* (2013.01); *G06K 9/00* (2013.01); *A61B 5/02416* (2013.01); *G01R 23/16* (2013.01)

(58) Field of Classification Search
CPC . A61B 5/7257; A61B 5/04012; A61B 5/7203; A61B 5/0402
USPC ......................................................... 600/513
See application file for complete search history.

(56) References Cited

U.S. PATENT DOCUMENTS

| | | | |
|---|---|---|---|
| 6,654,623 B1 | 11/2003 | Kastle | |
| 8,172,764 B2 | 5/2012 | Gregson et al. | |
| 2012/0289848 A1 | 11/2012 | Li et al. | |
| 2013/0127708 A1* | 5/2013 | Jung | A61B 5/0006 345/156 |
| 2014/0288452 A1 | 9/2014 | Mittal | |

FOREIGN PATENT DOCUMENTS

| | | |
|---|---|---|
| JP | 2000-262523 A | 9/2000 |
| JP | 2007-244478 A | 9/2007 |
| KR | 10-1048763 B1 | 7/2011 |
| KR | 10-1409452 B1 | 7/2014 |
| KR | 10-1426591 B1 | 8/2014 |

\* cited by examiner

*Primary Examiner* — Amanda K Hulbert
*Assistant Examiner* — Philip C Edwards
(74) *Attorney, Agent, or Firm* — NSIP Law

(57) ABSTRACT

A method of processing a biosignal includes estimating a time period from a time-domain biosignal, converting a biosignal corresponding to a time interval based on the time period to a frequency-domain signal, performing signal processing to remove a distortion component from the frequency-domain signal, and converting a processed frequency-domain signal obtained through the signal processing to a time-domain signal.

34 Claims, 13 Drawing Sheets

900

METHOD AND APPARATUS FOR PROCESSING BIOSIGNAL

CROSS-REFERENCE TO RELATED APPLICATIONS

This application claims the benefit under 35 USC 119(a) of Korean Patent Application No. 10-2015-0181555 filed on Dec. 18, 2015, in the Korean Intellectual Property Office, the entire disclosure of which is incorporated herein by reference for all purposes.

BACKGROUND

1. Field

The following description relates to a method and apparatus for processing a biosignal.

2. Description of Related Art

Recently, due to an aging population structure, increasing medical costs, and a lack of professional personnel engaged in medical services, research has been conducted on information technology (IT)-healthcare convergence technology in which IT is applied to medical technology. Thus, monitoring a health condition of an individual may be enabled anywhere, for example, at home and work, during daily life. For example, monitoring a health condition of a user may be enabled through mobile healthcare.

A biosignal may indicate a health condition of an individual. The biosignal may be, for example, an electrocardiogram (ECG) signal, a photoplethysmogram (PPG) signal, or an electromyogram (EMG) signal. Biosignals such as an ECG signal and a PPG signal may be associated with a periodic movement of a heart. Thus, unlike an EMG signal indicated only at a point in time when a muscle moves, biosignals associated with a periodic movement of a heart may have a waveform repeating in each time interval in a stable condition.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method of processing a biosignal includes estimating a time period from a time-domain biosignal, converting a biosignal corresponding to a time interval based on the time period to a frequency-domain signal, performing signal processing to remove a distortion component from the frequency-domain signal, and converting a processed frequency-domain signal obtained through the signal processing to a time-domain signal.

The biosignal may have a form in which a basic waveform of the time period is repeated.

The performing of the signal processing may include obtaining a first frequency component from the frequency-domain signal based on a determined number of times the basic waveform of the biosignal repeats during the time interval and removing, from the frequency-domain signal, a second frequency component corresponding to a remainder excluding the first frequency component.

The obtaining of the first frequency component may include extracting, from the frequency-domain signal, frequency components corresponding to an integer multiple of the number of times the basic waveform of the biosignal repeats during the time interval.

The first frequency component may include frequency components corresponding to an integer multiple of an inverse value of the time period.

The removing of the second frequency component may include setting, to a conjugate value, second frequency components at symmetrical frequencies in a frequency domain of the frequency-domain signal.

The removing of the second frequency component may include setting the second frequency component to zero.

The time interval may correspond to an integer multiple of the time period.

The converting of the biosignal to the frequency-domain signal may include extracting the biosignal corresponding to the time interval, and converting the extracted biosignal to the frequency-domain signal based on the number of times the basic waveform of the biosignal repeats during the time interval.

The converting of the extracted biosignal to the frequency-domain signal may include converting the extracted biosignal to the frequency-domain signal using at least one of a discrete Fourier transform (DFT) or a fast Fourier transform (FFT).

The converting of the processed frequency-domain signal to the time-domain signal may include converting the processed frequency-domain signal to the time-domain signal using at least one of an inverse DFT (IDFT) and an inverse FFT (IFFT).

The method may further include receiving the time-domain biosignal from an electrocardiogram (ECG), photoplethysmogram (PPG) or electromyogram (EMG) biosignal sensor.

A non-transitory computer-readable storage medium may include programmed instructions configured to cause a processor to perform one or more methods of processing a biosignal discussed herein.

In another general aspect, an apparatus for processing a biosignal includes a transmitting or receiving interface configured to receive a time-domain biosignal, and a processor configured to estimate a time period from the time-domain biosignal, convert a biosignal corresponding to a time interval based on the time period to a frequency-domain signal, perform signal processing to remove a distortion component from the frequency-domain signal, and convert a processed frequency-domain signal obtained through the signal processing to a time-domain signal.

The biosignal may have a form in which a basic waveform of the time period is repeated.

The processor may be further configured to obtain a first frequency component from the frequency-domain signal based on a determined number of times the basic waveform of the biosignal repeats during the time interval, and remove a second frequency component corresponding to a remainder excluding the first frequency component from the frequency-domain signal.

The processor may be further configured to extract, from the frequency-domain signal, frequency components corresponding to an integer multiple of the number of times the basic waveform of the biosignal repeats during the time interval.

The first frequency component may include frequency components corresponding to an integer multiple of an inverse value of the time period.

The processor may be further configured to set, to a conjugate value, second frequency components at symmetrical frequencies in a frequency domain of the frequency-domain signal.

The processor may be further configured to set the second frequency component to zero.

The time interval may correspond to an integer multiple of the time period.

The processor may be further configured to extract the biosignal corresponding to the time interval, and convert the extracted biosignal to the frequency-domain signal based on a determined number of times the basic waveform of the biosignal repeats during the time interval.

The processor may be further configured to convert the extracted biosignal to the frequency-domain signal using at least one of DFT or an FFT.

The processor may be further configured to convert the processed frequency-domain signal to the time-domain signal using at least one of an IDFT or an IFFT.

Other features and aspects will be apparent from the following detailed description, the drawings, and the claims.

BRIEF DESCRIPTION OF THE DRAWINGS

Throughout the drawings and the detailed description, the same drawing reference numerals refer to the same elements. The drawings may not be to scale, and the relative size, proportions, and depiction of elements in the drawings may be exaggerated for clarity, illustration, and convenience.

DETAILED DESCRIPTION

Figure 1:
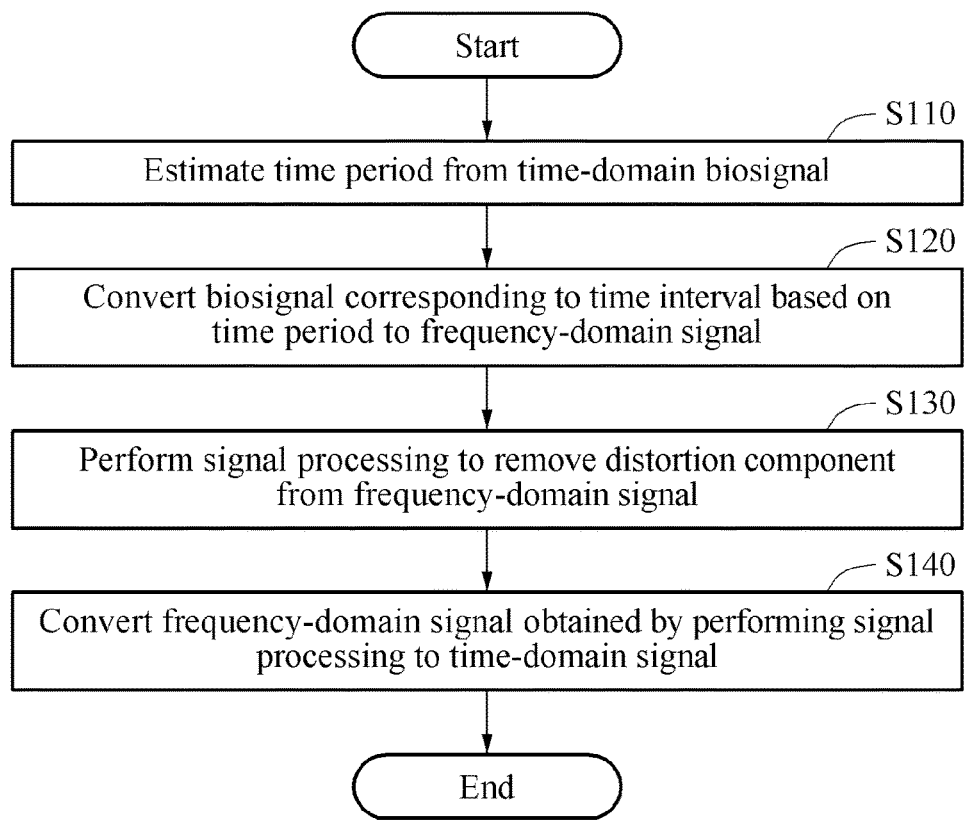
FIG. 1 is a flowchart illustrating an example of a method of processing a biosignal.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing particular examples only, and is not intended to limit the disclosure. As used herein, the singular forms "a," "an," and "the" are intended to include the plural forms as well, unless the context clearly indicates otherwise.

Terms such as first, second, A, B, (a), (b), and the like may be used herein to describe components. Each of these terminologies is not used to define an essence, order, or sequence of a corresponding component but used merely to distinguish the corresponding component from other component(s). For example, a first component may be referred to a second component, and similarly the second component may also be referred to as the first component.

It should be noted that if it is described in the specification that one component is "connected," "coupled," or "joined" to another component, a third component may be "connected," "coupled," and "joined" between the first and second components, although the first component may be directly connected, coupled, or joined to the second component. In addition, it should be noted that if it is described in the specification that one component is "directly connected" or "directly joined" to another component, a third component may not be present therebetween. Likewise, expressions, for example, "between" and "immediately between" and "adjacent to" and "immediately adjacent to" may also be construed as described in the foregoing.

One or more examples to be described hereinafter may be used to evaluate an exercise capability of a user. The examples may be provided in various devices such as, for example, a personal computer (PC), a laptop computer, a tablet computer, a smartphone, a smart home appliance, and a wearable device. One or more examples may be used to evaluate the exercise capability of the user using a heart rate measured from the user by, for example, a smartphone, a mobile device, a smart home system, or a wearable device, and to provide an exercise program suitable for the user. The examples may also be used to provide a healthcare service to the user. Hereinafter, examples are described in detail with reference to the accompanying drawings. In the following examples, known functions or configurations will be omitted.

FIG. 1 is a flowchart illustrating an example of a method of processing a biosignal. Methods of processing a biosignal, hereinafter simply referred to as "biosignal processing method," may be performed by apparatuses for processing a biosignal, hereinafter simply referred to as "processing apparatuses." The processing apparatuses include one or more processing devices configured to implement any, or any combination of, such biosignal processing methods.

Referring to FIG. 1, in operation S110, a processing apparatus estimates a time period (e.g., a period in which a signal cycle is completed) from a time-domain biosignal. The biosignal may have a form in which a basic waveform of the time period is repeated. Examples of the time-domain biosignal will be described with reference to FIGS. 2 through 6.

In operation S120, the processing apparatus converts a biosignal corresponding to a preset time interval based on the time period to a frequency-domain signal. The time interval may be a time interval corresponding to a multiple of the time period. For example, in operation S120, the processing apparatus may convert the biosignal to the frequency-domain signal using a discrete Fourier transform (DFT) and/or a fast Fourier transform (FFT). Example results of converting a biosignal to a frequency-domain signal by the processing apparatus will be described with reference to FIGS. 4, 5, and 7.

In operation S130, the processing apparatus performs signal processing to remove a distortion component from the frequency-domain signal. A detailed process of performing signal processing by the processing apparatus will be described with reference to FIG. 8.

In operation S140, the processing apparatus converts, to a time-domain signal, the frequency-domain signal obtained through the signal processing performed in operation S130. A result of converting a frequency-domain signal to a time-domain signal, or reconstructing the time-domain signal from the frequency-domain signal, by a processing apparatus will be described with reference to FIG. 9.

Mathematical induction processes that may be used to process a biosignal will be described with reference to FIGS. 2 through 5.

Figure 2:
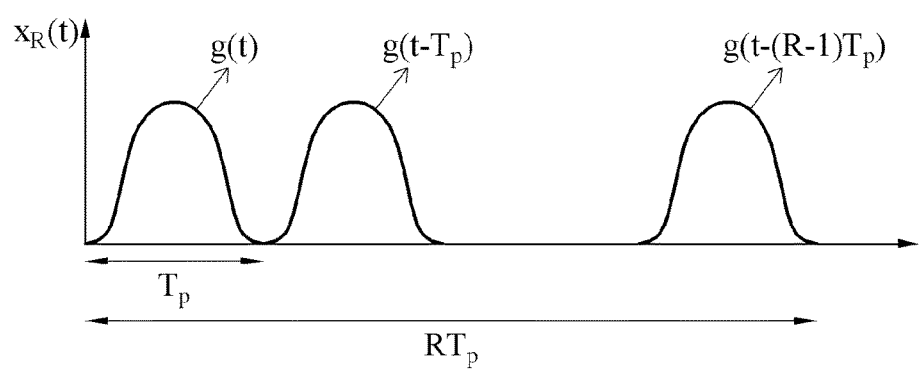
FIG. 2 is a diagram illustrating an example of a waveform of a biosignal.

FIG. 2 is a diagram illustrating an example of a waveform of a biosignal. In FIG. 2, a biosignal having a basic waveform g(t) is illustrated as an example of a biosignal having a repetitive waveform in a time domain.

In general, a biosignal in a stable state may have a periodically repeated waveform. For example, when it is assumed that such a waveform of a biosignal is truncated at a front and a back side, the waveform may be indicated as a form in which a pulse, for example, a basic waveform g(t), is repeated R times as illustrated in FIG. 2.

Referring to the graph of FIG. 2, a horizontal axis indicates a time (t), and a vertical axis indicates a magnitude, or an amplitude, of a signal $x_R(t)$ of which a waveform g(t) is repeated R times. The signal $x_R(t)$ of which the waveform g(t) is repeated R times as illustrated in the graph of FIG. 2 may be represented by Equation 1 below, for example.

$$x_R(t) = \sum_{r=0}^{R-1} g(t - rT_p) = \qquad [\text{Equation 1}]$$
$$g(t) + g(t - T_p) + g(t - 2T_p) + \ldots + g(t - (R-1)T_p)$$

In Equation 1, "$T_p$" denotes a time duration of the waveform g(t) that is periodically indicated. That is, $T_p$ denotes a time period (or "period") in which the signal completes a cycle. "R" denotes the number of times the waveform g(t) is repeated during a time interval.

Figure 3:
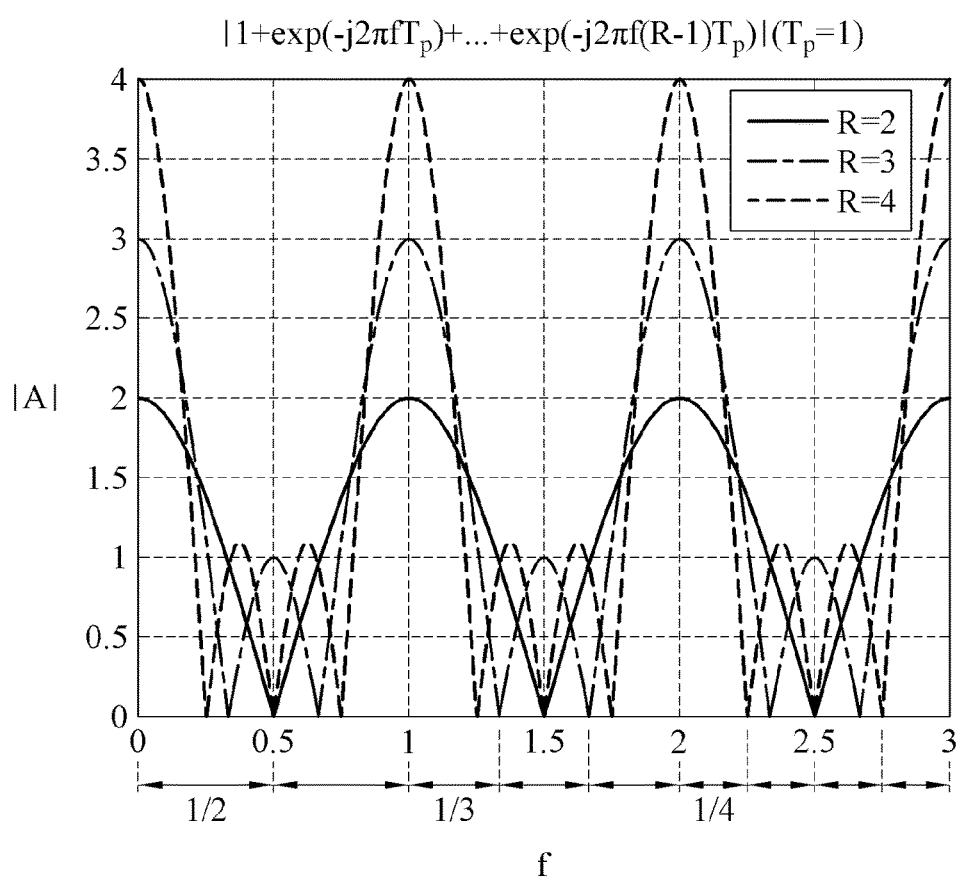
FIG. 3 is a graph illustrating an example of a result of converting a time-domain biosignal to a frequency-domain signal.

FIG. 3 is a graph illustrating an example of a portion of a result of converting a time-domain biosignal to a frequency-domain signal.

A result $X_R(f)$ obtained by converting a time-domain signal $x_R(t)$ to a frequency-domain signal by performing a Fourier transform on the time-domain signal $x_R(t)$ may be represented by Equation 2 below, for example.

$$X_R(f) = \qquad [\text{Equation 2}]$$
$$\sum_{r=0}^{R-1} G(f)\exp(-j2\pi f(rT_p)) = G(f)\sum_{r=0}^{R-1} \exp(-j2\pi f(rT_p))$$

In Equation 2, "G(f)" denotes a result of performing a Fourier transform on a waveform g(t), for example, $G(f) = \int_{-\infty}^{\infty} g(t)\exp(-j2\pi ft)dt$. The expression $$\text{``}\sum_{r=0}^{R-1} \exp(-j2\pi f(rT_p))\text{''}$$

on the right side of Equation 2 denotes an amplitude scaling factor A to be multiplied with G(f) to obtain the result $X_R(f)$ in a frequency domain.

In an example, when components other than a frequency component corresponding to an integer multiple of a period value are obtained as a value that is not zero due to a distortion component included in the time-domain signal $x_R(t)$, a processing apparatus may forcefully set the obtained value to zero to remove these other components.

In the example of FIG. 3, when a time period $T_p$ of the waveform g(t) is 1, and the number of repetitions R is 2, 3, and 4, an amplitude scaling factor, that is an amplitude |A| or $$\left|\sum_{r=0}^{R-1} \exp(-j2\pi f(rT_p))\right|,$$

of the result $X_R(f)$ obtained by the Fourier transform is illustrated. Referring to the graph of FIG. 3, a value of $$\left|\sum_{r=0}^{R-1} \exp(-j2\pi f(rT_p))\right|$$

may have R−1 0s between two neighboring peak values. In a case of a signal having a waveform repeated R times, a corresponding frequency spectral feature may indicate that, when a frequency changes by an integer multiple of (1/$T_p$), R−1 0s may be indicated at same intervals between neighboring frequencies.

The result $X_R(f)$ obtained through the Fourier transform based on the foregoing may be represented again by Equation 3 below, for example.

$$X_R(f) = \qquad [\text{Equation 3}]$$
$$\begin{cases} G(f) \cdot R, & \text{if } f = k/(RT_p) \text{ and } k = Rm \ (m: \text{interger}) \\ 0, & \text{if } f = k/(RT_p) \text{ and } k \neq Rm \ (m, k: \text{interger}) \\ G(f) \cdot (1 - \exp(-j2\pi fRT_p))/(1 - \exp(-j2\pi fT_p)), & \text{else} \end{cases}$$

In Equation 3, when m denotes an integer and a frequency f is $m/T_p$, $X_R(f) = G(f) \cdot R$. When f is $(Rm+1)/(RT_p)$, $(Rm+2)/(RT_p)$, . . . , $(Rm+R-1)/(RT_p)$, occurring at equidistant intervals between $m/T_p$ and $(m+1)/T_p$, $X_R(f)=0$. Here, the frequency f occurring at equidistant intervals between $m/T_p$ and $(m+1)/T_p$ may indicate a value obtained by dividing an interval between two frequency values, for example, $m/T_p$ and $(m+1)/T_p$, into R intervals, and corresponding to a total of R−1 frequency values.

Figure 4:
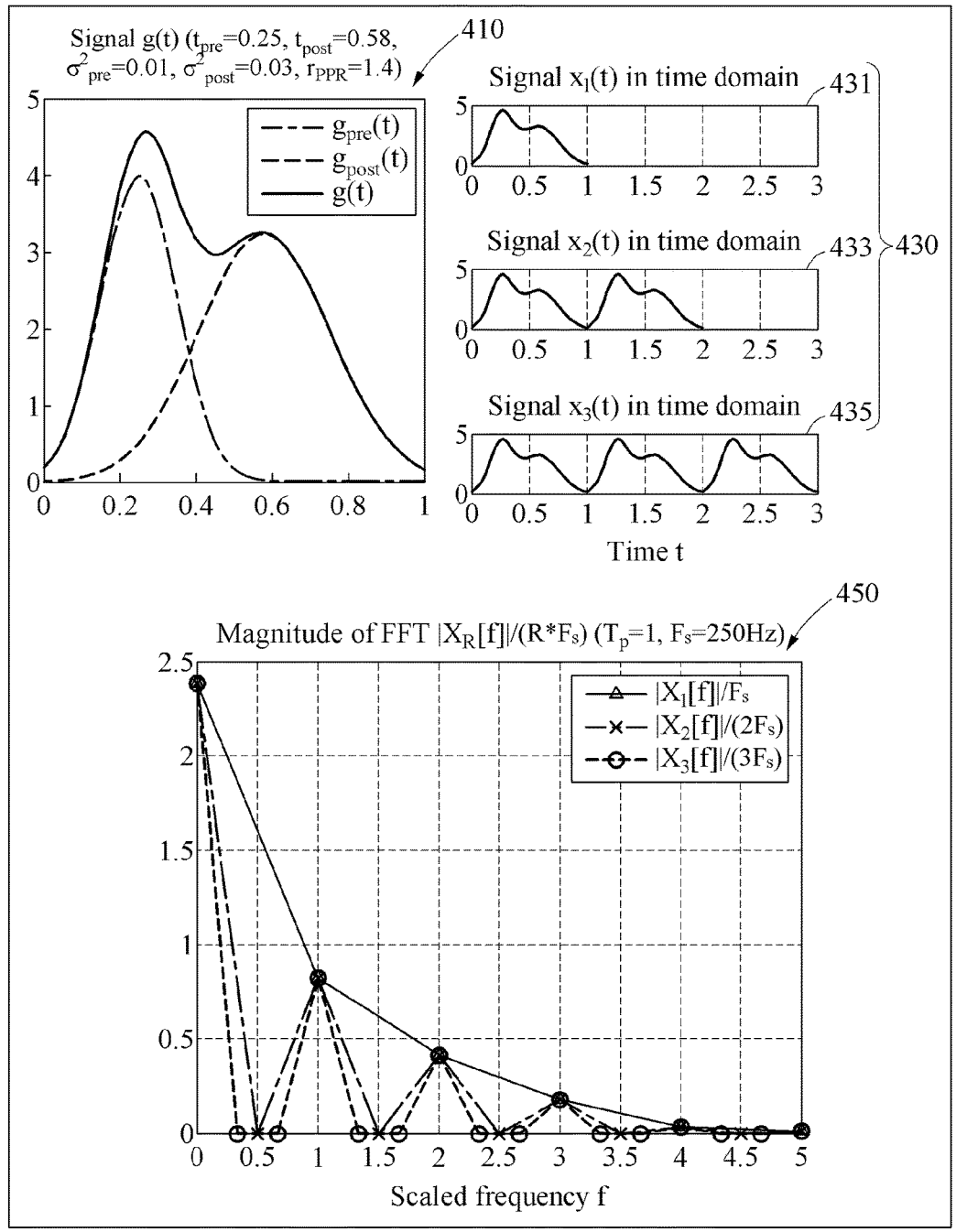
FIG. 4 is a diagram illustrating an example of a basic waveform of a biosignal, an example of a time-domain signal, and an example of a result of converting a time-domain biosignal to a discrete frequency-domain signal.

FIG. 4 is a diagram illustrating an example of a basic waveform of a biosignal, an example of a time-domain signal, and an example of a result of converting the time-domain signal to a discrete frequency-domain signal.

A biosignal may be output to be in a form of discrete digital values, and thus a processing apparatus may use a DFT corresponding to a discrete-time signal frequency analysis, instead of using a continuous-time Fourier transform corresponding to a continuous-time signal frequency analysis. Depending on an example, the processing apparatus may use an FFT that has an increased operation speed from the DFT. A resulting value from the DFT or the FFT may correspond to a value obtained by dividing a sampling value in a frequency domain by a sampling interval in a time domain, in the continuous-time Fourier transform.

Based on $X_R(f)$ described above, a resulting value $X_R[k]$ from such a DFT or FFT may be represented by Equation 4 below, for example.

$$X_R[k] = (1/T_s) \cdot X_R(f)|_{f=k/(NT_s)} = (1/T_s) \cdot X_R(f)|_{f=k/(RT_p)} \quad \text{[Equation 4]}$$

$$= \begin{cases} (1/T_s) \cdot R \cdot G(k/(RT_p)), \\ \text{for } k = Rm (m = 0, 1, 2, \ldots) \\ 0, \text{else} \end{cases}$$

In Equation 4, "$T_s$" denotes a sampling time interval used to convert a biosignal to a digital signal through sampling. A value of "k", which is an index, is an integer in a range of 0 k N−1, wherein a value of "N" denotes the number of overall samplings in a time domain and corresponds to a size or a length when performing the FFT. As indicated in Equation 4, the resulting value $X_R[k]$ from the DFT or the FFT may be zero, not a value at which an index k value corresponds to an integer multiple of R.

In FIG. 4, a time-domain biosignal 430 in which a basic waveform 410 is repeated one, two, and three times, and a result 450 obtained by converting the biosignal 430 to a frequency-domain signal through an FFT are illustrated.

Referring to FIG. 4, a signal 431, a signal 433, and a signal 435, which are signals in a time domain, are assumed for three cases in which the number of repetitions R of a function g(t) corresponding to the basic waveform 410 is set to 1, 2, and 3, respectively, based on the function g(t).

The result 450 may be obtained by converting each of the time-domain signals, for example, the signal 431, the signal 433, and the signal 435, through a DFT or the FFT.

The result 450 may correspond to a value obtained by dividing, by a value of $RF_s$, the resulting value $X_R[k]$ from the DFT or FFT for normalization.

In FIG. 4, a horizontal axis indicates a scaled value of k, for example, $k/(NT_s)$ corresponding to a discrete-time frequency.

In addition, "$F_s$" denotes an inverse value of $T_s$, and corresponds to a sampling rate in the time domain. $F_s$ may be, for example, 250 hertz (Hz).

Referring to a characteristic of the resulting value $X_R[k]$ from the DFT or the FFT that is discretely distributed, a value of $X_R[k]$ that is not 0 may be present at values of k corresponding to an integer multiple of R, and the value of $X_R[k]$ may be 0 at values of k therebetween.

For example, when the function g(t) is not repeated in an exactly the same form, but gradually changes over time by a motion artifact or irregularly changes by white noise, the value of $X_R[k]$ may not be 0 among values of k corresponding to an integer multiple of R, which may be represented by Equation 5 below, for example.

$$x_R(t) = \sum_{r=0}^{R-1} \{g(t - rT_p) + n_r(t - rT_p)\} \quad \text{[Equation 5]}$$

$$= g(t) + n_0(t) + g(t - T_p) + n_1(t - T_p) + \ldots +$$

$$g(t - (R-1)T_p) + n_{R-1}(t - (R-1)T_p)$$

In Equation 5, "$n_r(t-rT_p)$" denotes a non-repetitive component, considering all abnormal distortions when the function g(t) is not repeated in an exactly the same form. Here, an abnormal distortion may occur by, for example, an abnormal component that gradually changes in an r-th time interval or a high-frequency noise component that changes irregularly. When such an abnormal distortion occurs, the resulting value $X_R[k]$ obtained by performing the DFT or the FFT on the discrete-time signal obtained by sampling the signal $x_R(t)$ may be represented by Equation 6 below, for example.

$$X_R[k] = (1/T_s) \cdot X_R(f)|_{f=k/(NT_s)} = (1/T_s) \cdot X_R(f)|_{f=k/(RT_p)} \quad \text{[Equation 6]}$$

$$= \begin{cases} (1/T_s) \cdot \left[ R \cdot G(k/(RT_p)) + \sum_{r=0}^{R-1} N_r(k/(RT_p)) \right], \\ \text{for } k = Rm (m = 0, 1, 2, \ldots) \\ (1/T_s) \cdot \sum_{r=0}^{R-1} N_r(k/(RT_p)) \exp(-j2\pi kr/R), \text{else} \end{cases}$$

In Equation 6, "Nr(f)" is defined as $\int_{-\infty}^{\infty} n_r(t)\exp(-j2\pi ft) dt$, which indicates that the value of $X_R[k]$ may not be zero in a frequency component in which a value of k is not an integer multiple of R by components that are not 0, for example, $$(1/T_s) \cdot \sum_{r=0}^{R-1} N_r(k/(RT_p)) \exp(-j2\pi kr/R).$$

A change in a value of $X_R[k]$ based on a value of k will be described with reference to FIG. 5.

Figure 5:
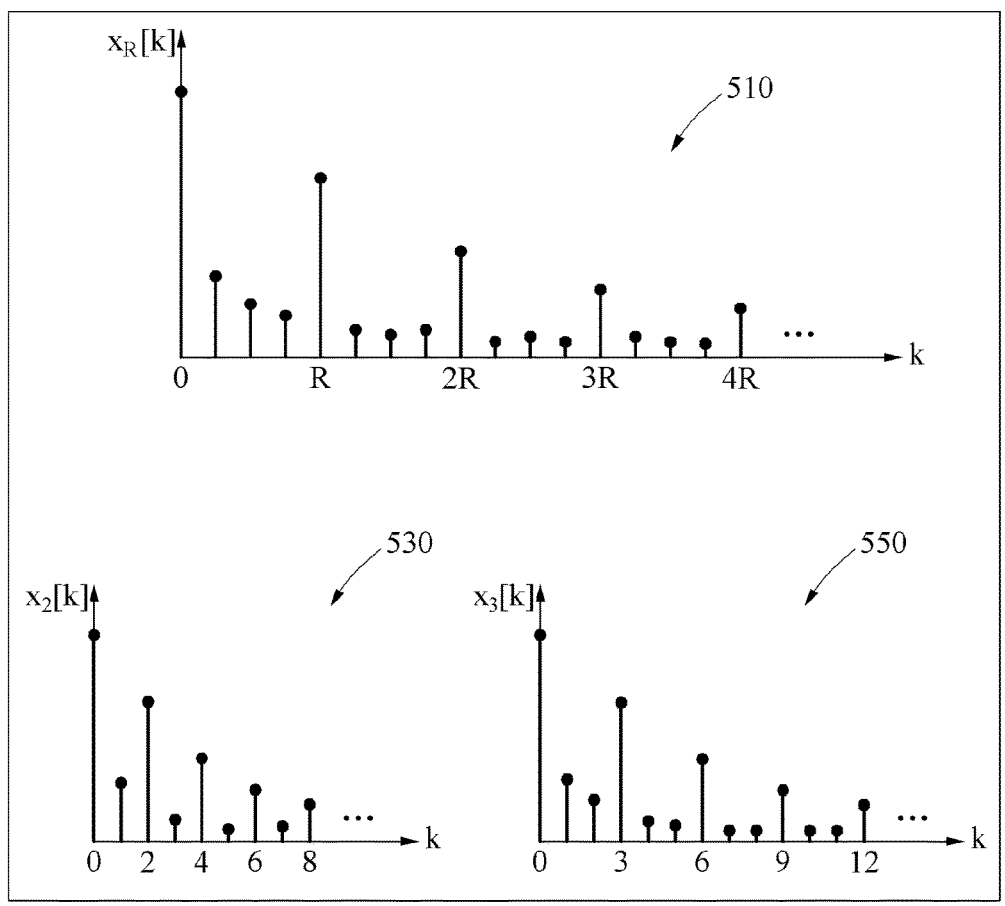
FIG. 5 is a diagram illustrating an example of a result of converting a waveform including a distortion component, and repeated R times, to a frequency-domain signal.

FIG. 5 is a diagram illustrating an example of a result of converting a waveform including a distortion component and repeated R times to a frequency-domain signal. In FIG. 5, a result 510 is obtained by conversion performed based on a value of R being 4 (R=4), a result 530 is obtained by conversion based on a value of R being 2 (R=2) and a result 550 is obtained by conversion based on a value of R being 3 (R=3).

Referring to the result 510, a relatively high frequency spectrum is indicated at each integer multiple of 4, and frequency spectrums present therebetween indicate a value that is not zero due to an abnormal distortion component. Similarly, referring to the result 530 and the result 550, a relatively high frequency spectrum is indicated at each integer multiple of 2 and 3, respectively, and frequency spectrums present therebetween indicate a value that is not zero due to an abnormal distortion component.

In an example, a distortion of a biosignal by various abnormal components may be removed or reduced using a characteristic of a repetitive waveform of the biosignal and a result of converting the biosignal to a signal towards a frequency axis.

A detailed process of performing signal processing in a biosignal processing method will be described with reference to FIGS. 6 and 7.

Figure 6:
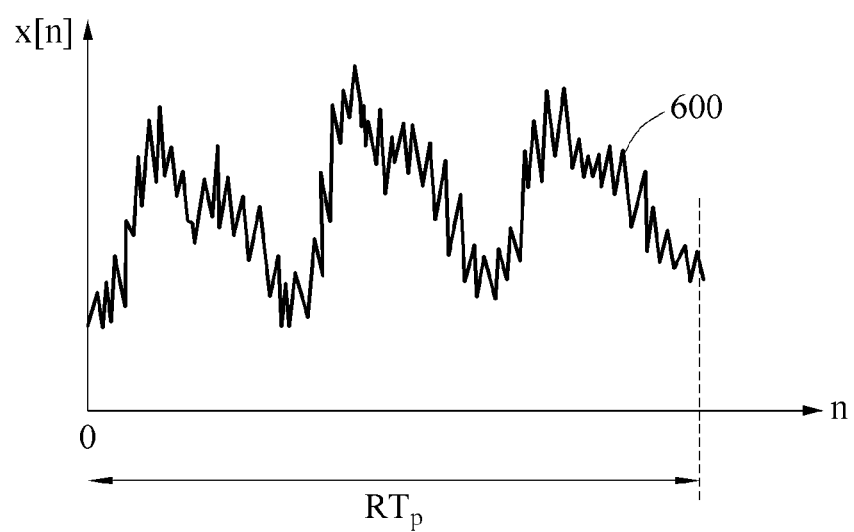
FIG. 6 is a diagram illustrating an example of a waveform of a biosignal including a distortion component.

FIG. 6 is a diagram illustrating an example of a waveform of a biosignal including a distortion component. In the example of FIG. 6, a waveform 600 of a biosignal x[n] in a time interval corresponding to a multiple of R of a time period $T_p$ estimated in a time axis or a time domain is illustrated. A magnitude of the waveform 600 of the biosignal x[n] is assumed to be x[n] (0≤n≤N−1).

A detailed process of estimating the time period $T_p$ will be described hereinafter.

For example, a processing apparatus may repeat a process of obtaining a minimum value and a maximum value of the biosignal x[n], in sequential order, based on a change in time, and may obtain Nt time values corresponding to the minimum value, wherein a value of Nt is less than 1 (Nt<1). The processing apparatus may estimate an approximate period by dividing, by a value of Nt−1, a total period of time used for intervals including time values corresponding to the minimum value.

For example, a waveform of a photoplethysmogram (PPG) biosignal in a time axis that is obtained as a result of setting R to 3 (R=3) may be assumed to be the waveform 600 of the biosignal x[n] as illustrated in FIG. 6.

Here, when the biosignal x[n] is converted to a frequency-domain signal through a DFT, a result X[k] may be obtained as represented by Equation 7 below, for example.

$$X[k] = \sum_{n=0}^{N-1} x[n]e^{-j(2\pi/N)kn}, \text{ for } 0 \leq k \leq N-1 \quad \text{[Equation 7]}$$

Figure 7:
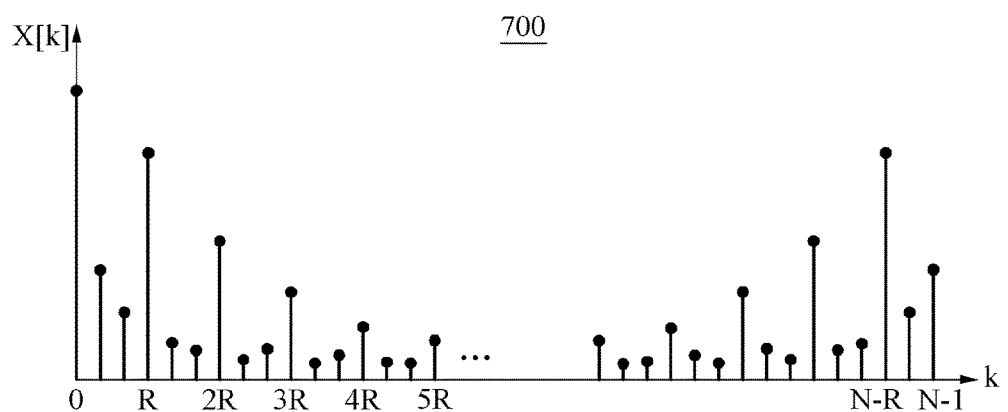
FIG. 7 is a diagram illustrating an example of a result of converting a biosignal including a distortion component to a frequency-domain signal.

The result X[k] obtained by performing the DFT on the waveform 600 of the biosignal x[n] is illustrated in FIG. 7

FIG. 7 is a diagram illustrating an example 700 of a result of converting a biosignal including a distortion component to a frequency-domain signal. More specifically, a result X[k] obtained by performing a DFT on a waveform of a biosignal x[n] is illustrated.

A processing apparatus may leave, from the frequency-domain signal obtained by the DFT, only $N_{rcn}$ frequency signal components, for example, a first frequency component, indicated at each integer multiple of a period value R corresponding to the number of repetitions. The first frequency component may include frequency components corresponding to an integer multiple of an inverse value of a time period.

The processing apparatus may set, to zero, all remaining frequency components, for example, a second frequency component, present between the frequency signal components indicated at each integer multiple of the period value R, as represented by Equation 8 below, for example.

$$X_{rcn}[k] = \begin{cases} X[k], \text{ for } k = R, 2R, \ldots, N_{rcn}R \\ \text{conj}(X[N-k]), \text{ for } k = N - N_{rcn}R, N - \\ (N_{rcn}-1)R, \ldots, N-R \\ 0, \text{ else} \end{cases} \quad \text{[Equation 8]}$$

In Equation 8, $X_{rcn}[k]$ is set to be equal to conj(X[N−k]), for example, $X_{rcn}[k]$=conj(X[N−k]), with respect to k=N−$N_{rcn}$R, N−($N_{rcn}$−1)R, • • • , N−R, due to the following reasons.

For example, when performing the DFT on a time-domain signal corresponding to a real number, frequency components at frequency locations that are symmetrical in both sides from a center of a graph of FIG. 7 may have a conjugate value.

In an example, such a feature of having a conjugate value may be applied to perform signal processing to set the remaining frequency components, or the second frequency component, present between the frequency signal components indicated at each integer multiple of the period value R.

The processing apparatus may use a value of X[k] when k=R, 2R, • • • , $N_{rcn}$R, and set the locations symmetrical in both sides from the center of a frequency axis to be corresponding values, for example, conjugate values.

Depending on an example, the processing apparatus may use the value of X[k] when k=R, 2R, • • • , $N_{rcn}$R, or k=N−$N_{rcn}$R, N−($N_{rcn}$−1)R, • • • , N−R, and set values of the remaining frequency components to zero.

Figure 8:
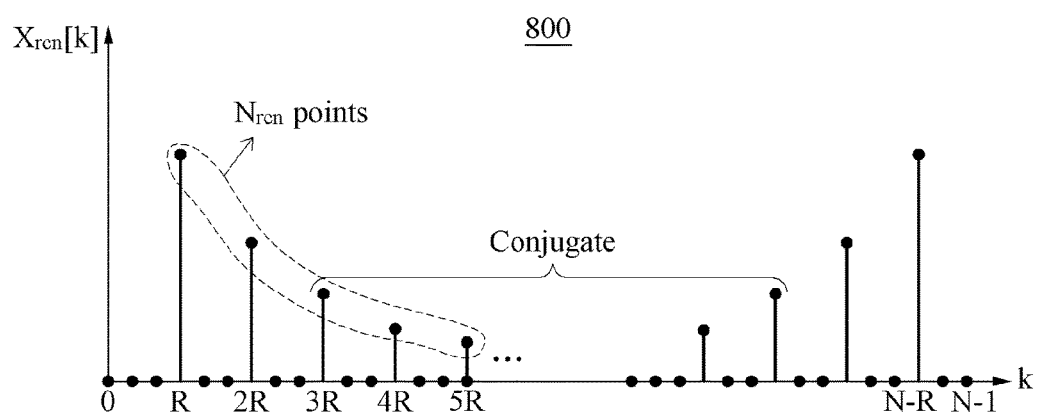
FIG. 8 is a diagram illustrating an example of a process of removing a distortion component from a frequency-domain signal obtained by conversion.

FIG. 8 is a diagram illustrating an example 800 of a process of removing a distortion component from a frequency-domain signal obtained by conversion. In the example of FIG. 8, a signal $X_{rcn}[k]$ reconstructed to be in a time domain by setting a value of $N_{rcn}$ to be equal to 4, for example, $N_{rcn}$=4, using a result X[k] obtained by performing a DFT on a waveform of a biosignal x[n] is illustrated.

A processing apparatus may perform signal processing to convert a frequency-domain signal obtained by conversion to a time-domain signal using an inverse DFT (IDFT) based on X[k] obtained as result of the DFT. As a result, the signal $X_{rcn}[k]$ reconstructed to be in the time domain may be represented by Equation 9 below, for example.

$$x_{rcn}[n] = \frac{1}{N}\sum_{k=0}^{N-1} X_{rcn}[k]e^{j(2\pi/N)kn}, \text{ for } 0 \leq n \leq N-1 \quad \text{[Equation 9]}$$

In Equation 9, the number of values of $X_{rcn}[k]$ that are not zero is $2N_{rcn}$.

Since the values of $X_{rcn}[k]$ have conjugate relationships based on the center of the frequency axis, the number of multiplications to be actually performed may be $N_{rcn}$, not N.

A value $x_{rcn}[n]$ obtained from Equation 9 may be a reconstructed time-domain biosignal from which a distortion signal is removed. The reconstructed signal may have a form in which a basic waveform is accurately repeated R times.

Figure 9:
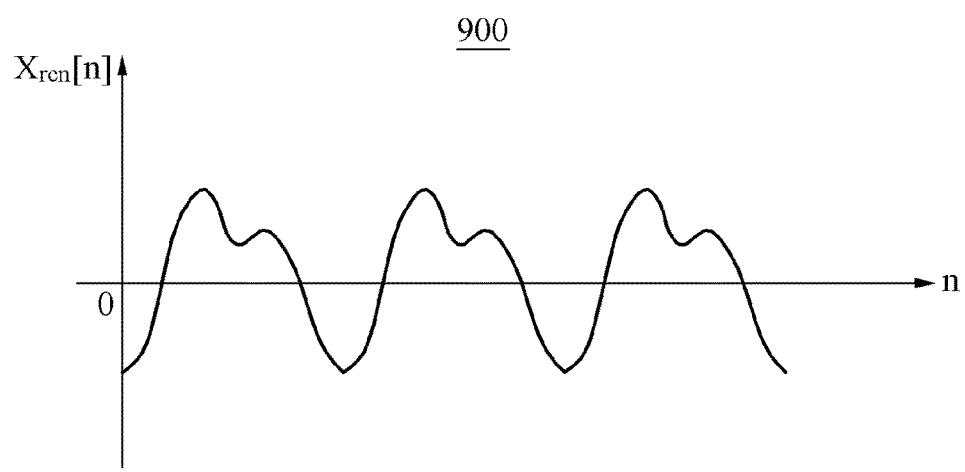
FIG. 9 is a diagram illustrating an example of a waveform of a signal reconstructed by removing a distortion component from a biosignal.

The processing apparatus may obtain $X_{rcn}[k]$ transformed from the result X[k] obtained by performing the DFT using the waveform of the biosignal x[n] distorted as illustrated in FIG. 6, and may obtain the final signal $x_{rcn}[n]$ reconstructed to be in the time domain and illustrated in FIG. 9.

FIG. 9 is a diagram illustrating an example 900 of a waveform of a biosignal $x_{rcn}[n]$ reconstructed by removing a distortion component from a biosignal x[n]. For example, an irregular biosignal that is distorted by a change in an unstable dynamic movement environment, an unstable human contact state, and occurrence of various types of noise may be reconstructed to be a smoothed signal.

In an example, a processing apparatus may use a repetitive form of a biosignal, and thus may not need to consider a settlement time of the biosignal for which the biosignal is settled and a phase distortion. In addition, the processing apparatus may use only a biosignal corresponding to a time interval, in lieu of all time intervals, and thus may minimize the number of frequency components and reduce a calculation complexity, and also minimize noise in a pass band.

Figure 10:
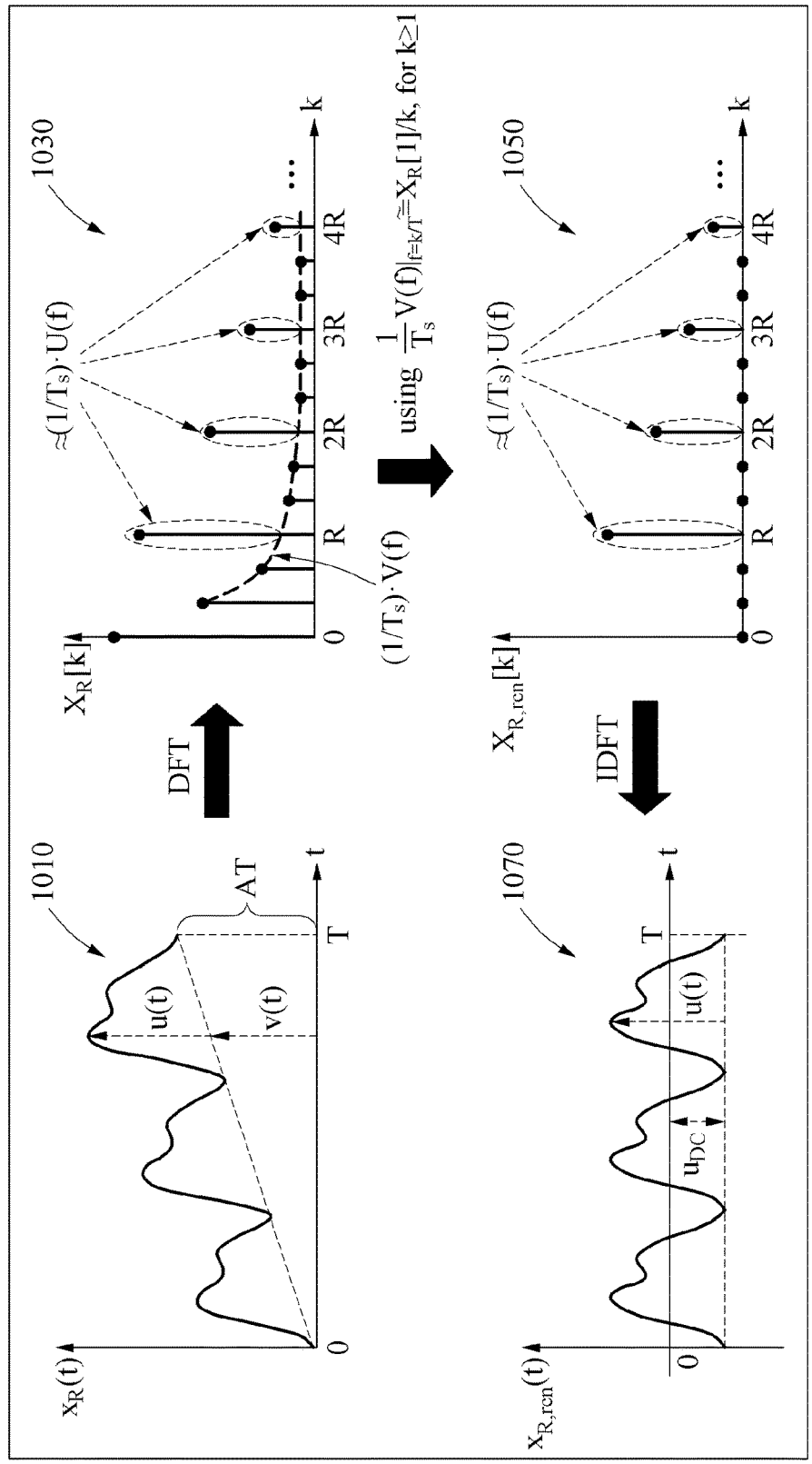
FIG. 10 is a diagram illustrating an example of a sequential method of performing signal processing to remove a distortion component from a biosignal.

FIG. 10 is a diagram illustrating an example of a sequential method of processing a biosignal to remove a distortion component from the biosignal. In the example of FIG. 10, processes in a method of processing a biosignal by a processing apparatus to remove a distortion component from the biosignal are illustrated in sequential order. More specifically, the processing apparatus processes a biosignal $x_R(t)$ 1010, wherein $x_R(t)=u(t)+v(t)$.

"u(t)" indicates a component to be detected for analyzing the biosignal $x_R(t)$ 1010 and may include an irregular noise component. "v(t)" indicates a component corresponding to a linear offset that is unnecessary for the detecting. Such a linear offset component may have a regular form, and thus may be estimated and removed through signal processing. The method described herein may additionally remove such an offset component of a regular form, in addition to irregular noise.

Referring to FIG. 10, in response to the biosignal $x_R(t)$ 1010, $x_R(t)=u(t)+v(t)$, being received, the processing apparatus converts the biosignal $x_R(t)$ 1010 to a frequency-domain signal $X_R[k]$ 1030 using a DFT.

The signal $X_R[k]$ 1030 may be represented by Equation 10 below, for example.

$$X_R[k] \approx (1/T_s) \cdot X_R(f)|_{f=k/T} = (1/T_s) \cdot (U(f)+V(f))|_{f=k/T}$$ [Equation 10]

In Equation 10, $k \leq N/2$. A frequency signal component, for example, a first frequency component, indicated at each integer multiple of a period value R corresponding to the number of repetition times of a waveform of the signal $X_R[k]$ 1030 may be similar to $(1/T_s) \cdot (U(f)+V(f))$. Here, a value of U(f) may include a desired value, but a value of V(f) may be a value corresponding to an undesired offset that may need to be removed. In addition, remaining frequency components, for example, second frequency components, present between the frequency signal components indicated at each integer multiple of the period value R may be values of $(1/T_s) \cdot V(f)$.

The processing apparatus obtains a reconstructed signal $X_{R,rcn}[k]$ 1050 obtained by removing the distortion component using $$\frac{1}{T_s} V(f)|_{f=k/T} \cong X_R[1]/k, \text{ for } k \geq 1.$$

Here, a magnitude of the first frequency component in the reconstructed signal $X_{R,rcn}[k]$ 1050 may be similar to a value of $(1/T_s) \cdot U(f)$.

The reconstructed signal $X_{R,rcn}[k]$ 1050 may be represented by Equation 11 below.

$$X_{R,rcn}[k] = \begin{cases} X_R[k] - X_R[1]/k, & \text{for } k = R, 2R, 3R, \ldots \\ 0, & \text{else} \end{cases}$$ [Equation 11]

The processing apparatus may convert the reconstructed signal $X_{R,rcn}[k]$ 1050 to a time-domain signal $x_{R,rcn}(t)$ 1070 again by an inverse DFT (IDFT). In the time-domain signal $x_{R,rcn}(t)$ 1070 that is finally obtained through the converting, an offset may be adjusted by a value of $u_{DC}$ as represented by "$x_{R,rcn}(t)=u(t)-u_{DC}$."

Figure 11:
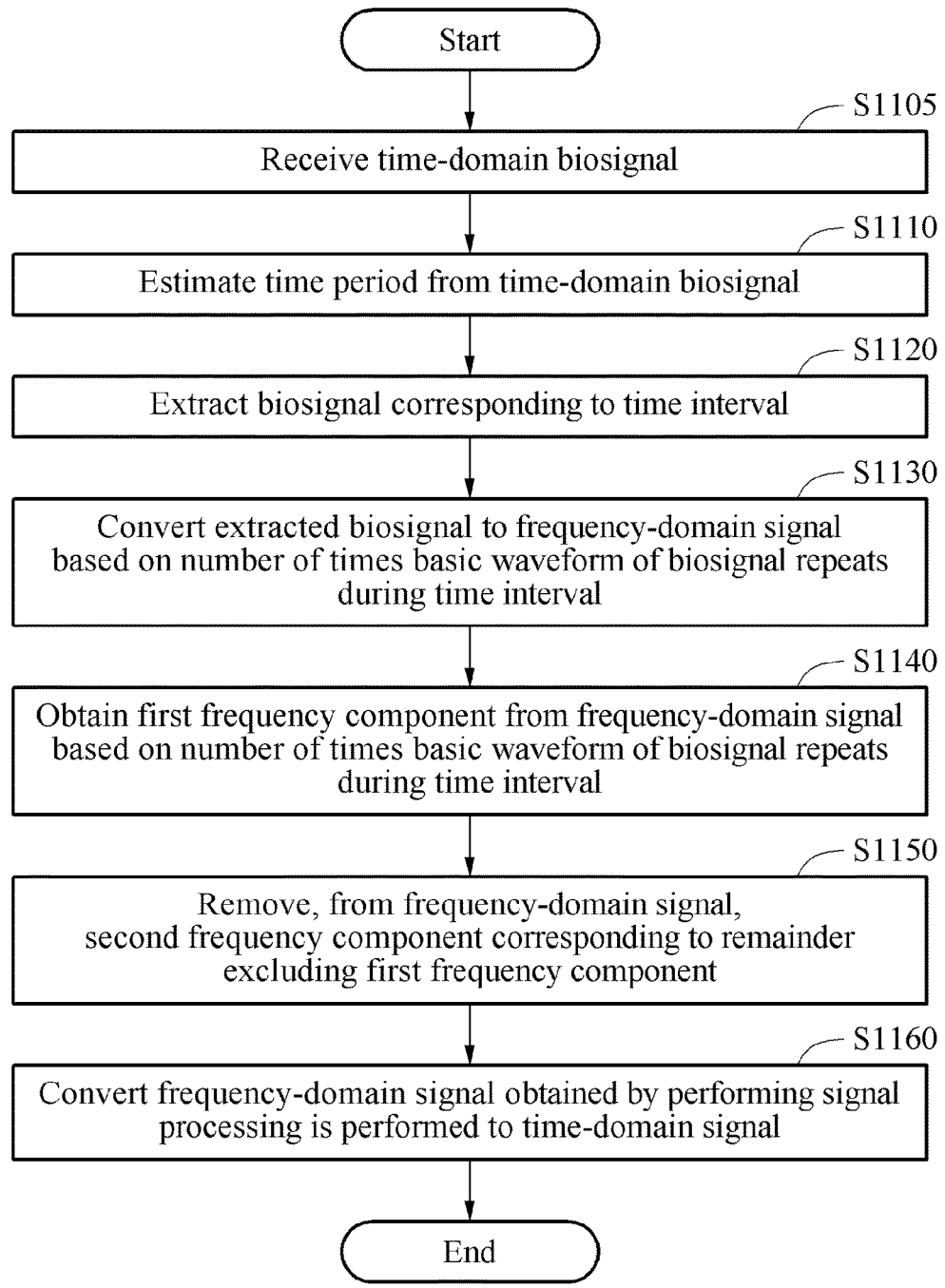
FIG. 11 is a flowchart illustrating another example of a method of processing a biosignal.

FIG. 11 is a flowchart illustrating another example of a biosignal processing method. Referring to FIG. 11, in operation S1105, a processing apparatus receives a time-domain biosignal. The processing apparatus may receive, from a wearable device or a mobile terminal, and/or from sensors of the included wearable device or mobile terminal that performs the example processing method, a biosignal measured or detected by the wearable device or the mobile terminal.

In operation S1110, the processing apparatus estimates a time period from the time-domain biosignal. The estimated time period is, for example, a time in which the time-domain biosignal completes a full cycle.

In operation S1120, the processing apparatus extracts a biosignal corresponding to a time interval corresponding to an integer multiple of the time period. In operation S1130, the processing apparatus converts the extracted biosignal to a frequency-domain signal based on the number of times a basic waveform of the biosignal repeats during the time interval. For example, the processing apparatus may convert the extracted biosignal to the frequency-domain signal using at least one of a DFT and an FFT.

The processing apparatus may remove a distortion component from the frequency-domain signal obtained by the converting in operation S1130. In operation S1140, the processing apparatus obtains a first frequency component from the frequency-domain signal based on the number of times the basic waveform of the biosignal repeats during the time interval. The processing apparatus may extract, from the frequency-domain signal, frequency components corresponding to an integer multiple of the number of repetitions. The first frequency component may include frequency components corresponding to an integer multiple of an inverse value of the time period.

In operation S1150, the processing apparatus removes, from the frequency-domain signal, a second frequency component corresponding to a remainder excluding the first frequency component. The processing apparatus may set the second frequency component to zero.

In operation S1160, the processing apparatus converts a frequency-domain signal obtained through signal processing to a time-domain signal.

Figure 12:
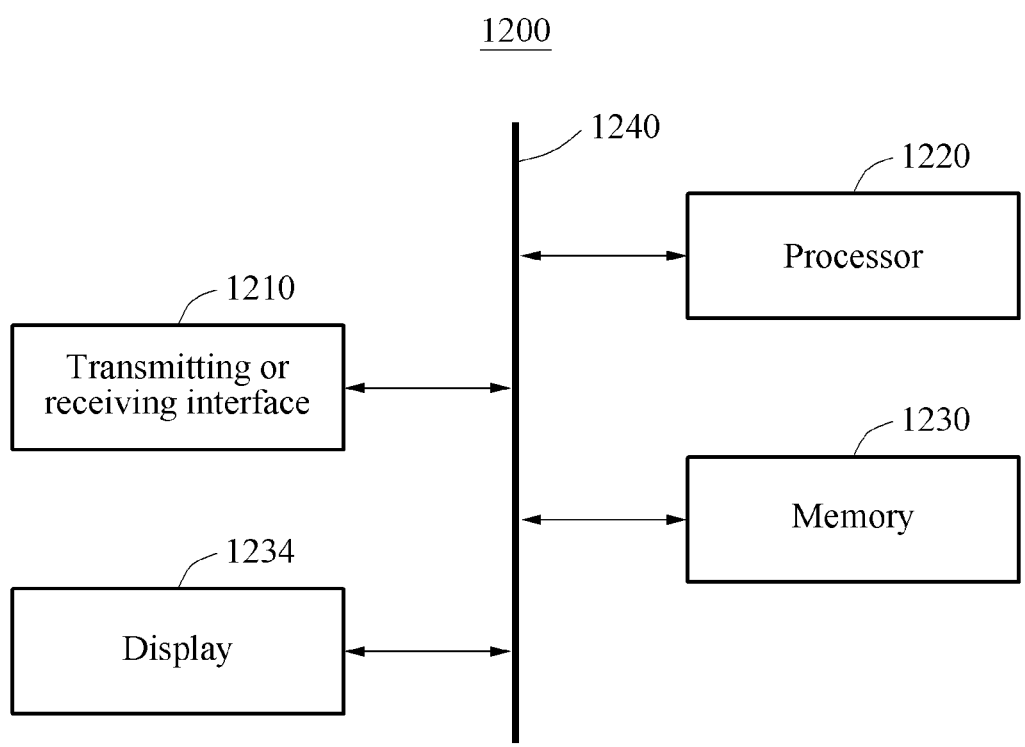
FIG. 12 is a diagram illustrating an example of an apparatus for processing a biosignal.

FIG. 12 is a diagram illustrating an example of a processing apparatus 1200. Referring to FIG. 12, the processing apparatus 1200 includes, for example, a transmitting or receiving interface 1210, a processor 1220, a memory 1230, a display 1234 and a bus 1240. The transmitting or receiving interface 1210, the processor 1220, the memory 1230 and the display 1234 may communicate with one another through the bus 1240.

The transmitting or receiving interface 1210 receives a time-domain biosignal. For example, the biosignal may include a repetitive waveform.

The transmitting or receiving interface 1210 may be, for example, a wireless Internet interface such as, for example, wireless local area network (WLAN), WiFi direct, digital living network alliance (DLNA), wireless broadband (Wi-Bro), worldwide interoperability for microwave access (Wi-MAX), and high-speed downlink packet access (HSDPA), and a near-field communication interface such as, for example, Bluetooth™, radio-frequency identification (RFID), infrared data association (IrDA), ultra-wideband (UWB), or near-field communication (NFC). The transmitting or receiving interface 1210 may include sensors to measure the biosignal, or such sensors may be included in a corresponding processing system where the sensors communicate with the apparatus through the transmitting or receiving interface 1210. The sensors may include ECG, PPG and/or EMG sensors controllable to measure the biosignal from a body.

The processor 1220 estimates a time period (e.g., a time in which the biosignal completes a full cycle) from the biosignal, and converts a biosignal corresponding to a time interval based on the time period to a frequency-domain signal. The processor 1220 extracts the biosignal corresponding to the time interval, and converts the extracted biosignal to the frequency-domain signal based on the number of times a basic waveform of the biosignal repeats during the time interval. According to an example, the time interval corresponds to an integer multiple of the time period, and the processor 1220 converts the extracted biosignal to the frequency-domain signal using a Fourier transform and a DFT.

The processor 1220 performs signal processing to remove a distortion component from the frequency-domain signal, and converts a frequency-domain signal obtained through the signal processing to a time-domain signal. The time interval may include a time interval corresponding to a multiple of the time period.

For example, in the signal processing to remove the distortion component, the processor 1220 obtains a first frequency component from the frequency-domain signal based on the number of times the basic waveform of the biosignal repeats during the time interval. The processor 1220 extracts, from the frequency-domain signal, frequency components corresponding to an integer multiple of the number of repetitions. The first frequency component may include frequency components corresponding to an integer multiple of an inverse value of the time period.

The processor 1220 removes, from the frequency-domain signal, a second frequency component corresponding to a remainder excluding the first frequency component. The processor 1220 sets the second frequency component to zero. The processor 1220 converts the frequency-domain signal resulting from the removal of the second frequency component (e.g., the signal including the first frequency component) to a time-domain signal using, for example, an IDFT and an IFFT.

In an example, the processor 1220 may output information of the time-domain signal resulting from the conversion of the frequency-domain signal to an output, such as, for example, the display 1234 of the processing apparatus 1200. The display 1234 may be a physical structure that includes one or more hardware components that provide the ability to display an image and/or information of the time-domain signal. The display 1234 may also be configured to display a rendered user interface and/or receive user input. The display 1234 can encompass any combination of display region, gesture capture region, a touch sensitive display, and/or a configurable area. The display 1234 can be embedded in the processing apparatus 1200 or may be an external peripheral device that may be attached and detached from the processing apparatus 1200. The display 1234 may be a single-screen or a multi-screen display. A single physical screen can include multiple displays that are managed as separate logical displays permitting different content to be displayed on separate displays although part of the same physical screen. The display 1234 may also be implemented as an eye glass display (EGD), which includes one-eyed glass or two-eyed glasses.

In addition, the processor 1220 may perform at least one method or process described with reference to FIGS. 1 through 11 and to be described with reference to FIG. 13. The processor 1220 may execute a program code that may control the processing apparatus 1200 to implement one or more processing methods described herein. Program code to be executed by the processor 1220 may be stored in the memory 1230 or another non-transitory medium. The processing apparatus 1200 may be connected to an external device, for example, a personal computer (PC) or a network, through an input or output device (not shown), and may exchange data between the external device and the input or output device.

At least one method or process described with reference to FIGS. 1 through 11 and to be described with reference to FIG. 13 may be embodied in a processor executing program code to implement such methods or processes in a tablet, a smartphone, or a wearable device, or in a form of a processing device or chip to be embedded in a smartphone or a wearable device configured to control the processor to implement such methods or processes.

Figure 13:
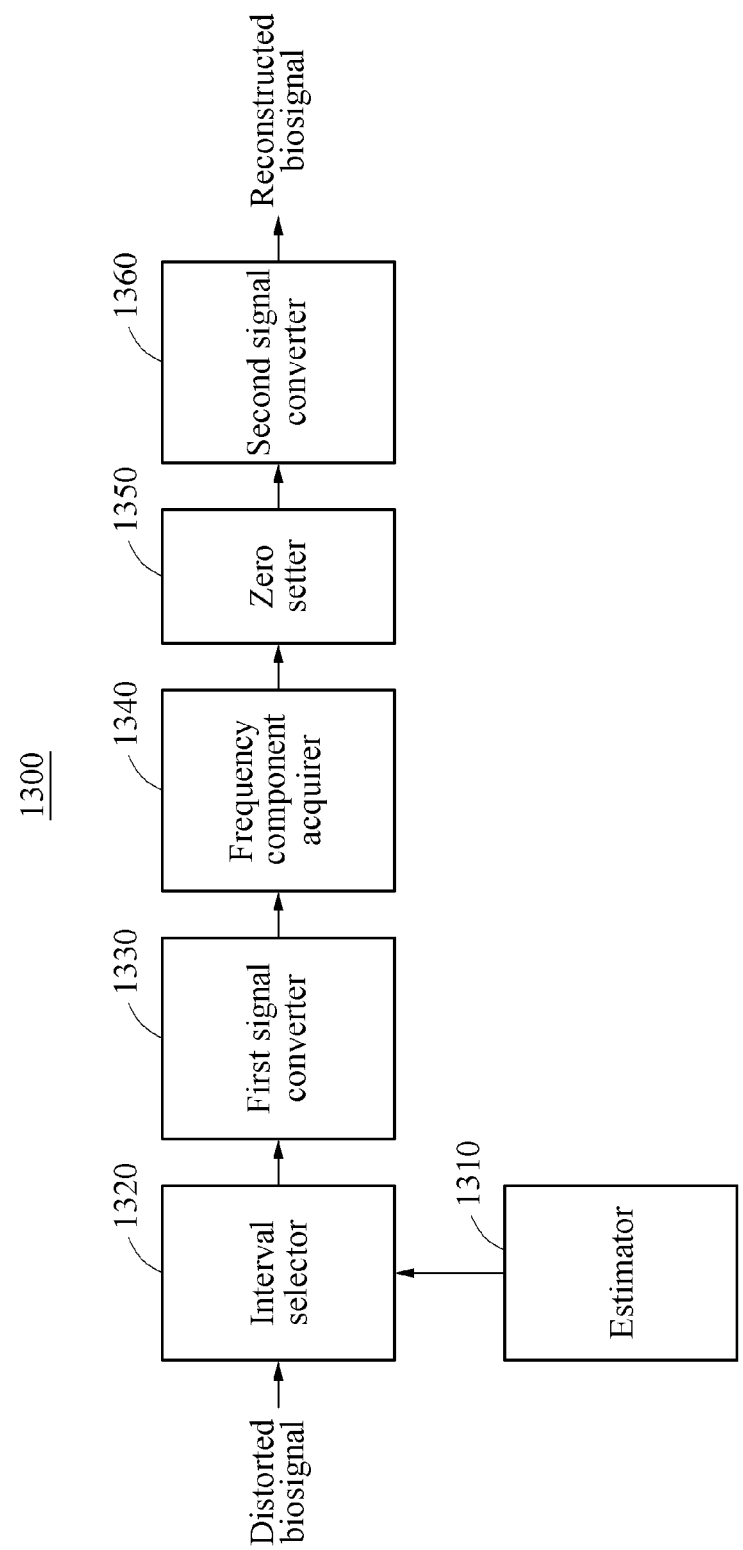
FIG. 13 is a diagram illustrating another example of an apparatus for processing a biosignal.

FIG. 13 is a diagram illustrating another example of a processing apparatus 1300. Referring to FIG. 13, the processing apparatus 1300 includes, for example, an estimator 1310, an interval selector 1320, a first signal converter 1330, a frequency component acquirer 1340, a zero setter 1350, and a second signal converter 1360.

The estimator 1310 estimates a time period of a received or detected time-domain biosignal. The estimated time period is, for example, a time in which the biosignal completes a full cycle. The received or detected biosignal may be an abnormal and distorted biosignal. The biosignal may have a form in which a basic waveform of the time period is repeated.

The interval selector 1320 selects a time interval of the time-domain biosignal. For example, the interval selector 1320 may select a time interval corresponding to a multiple of R of the time period.

The first signal converter 1330 converts, to a frequency-domain signal, the biosignal corresponding to a time interval corresponding to a multiple of R of the time period. The first signal converter 1330 may also be referred to as a frequency-domain signal converter. The first signal converter 1330 may convert the time-domain biosignal to the frequency-domain signal using, for example, a Fourier transform and a DFT.

According to an example, when converting the biosignal to the frequency-domain signal, the first signal converter 1330 may obtain only frequency components required for the frequency component acquirer 1340 without obtaining all frequency components.

The frequency component acquirer 1340 obtains a first frequency component from a frequency domain based on the number of times the basic waveform of the biosignal repeats during the time interval. Here, the number of frequency components to be obtained by the frequency component acquirer 1340 may be set to a finite value based on a complexity and accuracy.

When the number of the frequency components to be obtained by the frequency component acquirer 1340 increases, an accuracy of a signal to be reconstructed may increase, although a calculation complexity may also increase. To ensure a predetermined level of accuracy, the frequency component acquirer 1340 may determine an appropriate number of the frequency components to be obtained.

The zero setter 1350 sets all other frequency components to 0, excluding frequency components indicated at each frequency corresponding to an integer multiple of R from a result from the conversion to the frequency domain by the first signal converter 1330.

The second signal converter 1360 converts, to a time-domain signal, a frequency-domain signal, for example a frequency response obtained through the frequency component acquirer 1340 and the zero setter 1350. The second signal converter 1360 may also be referred to as a time-domain signal converter. The second signal converter 1360 may convert the frequency-domain signal to the time-domain signal using, for example, an IDFT and an IFFT.

After such an operation by the second signal converter 1360, a biosignal from which an abnormal distortion signal is removed may be reconstructed. The reconstructed biosignal may be a signal in which a basic waveform is accurately repeated R times in a time domain.

The apparatuses, units, modules, devices, and other components illustrated in FIGS. 12 and 13 (e.g., the transmitting or receiving interface 1210, processor 1220, memory 1230, bus 1240, estimator 1310, interval selector 1320, first signal converter 1330, frequency component acquirer 1340, zero setter 1350, and second signal converter 1360) that perform the operations described herein with respect to FIGS. 1-11 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1-11. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1 and 11 that perform the operations described herein with respect to FIGS. 2-10, 12 and 13 are performed by computing hardware, for example, by one or more processors or computers, as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A processor-implemented biosignal processing method, comprising:
   estimating a time period from a biosignal in a time-domain;
   converting, based on the time period, a biosignal corresponding to a time interval of the biosignal to a frequency-domain signal;
   performing signal processing by removing a determined distortion component from the frequency-domain signal; and
   generating a reconstructed time-domain biosignal, as a reconstruction of the biosignal corresponding to the time interval, by converting a processed frequency-domain signal, obtained through the signal processing, to the time-domain.

2. The method of claim 1, wherein the biosignal comprises a form in which a basic waveform is repeated in the biosignal during the time period.

3. The method of claim 1, wherein the time interval corresponds to an integer multiple of the time period.

4. The method of claim 1, wherein the converting of the biosignal corresponding to the time interval to the frequency-domain signal comprises:
   extracting the biosignal corresponding to the time interval from the biosignal; and
   converting the extracted biosignal to the frequency-domain signal based on a determined number of times a basic waveform of the biosignal repeats during the time interval.

5. The method of claim 4, wherein the converting of the extracted biosignal to the frequency-domain signal comprises:
   converting the extracted biosignal to the frequency-domain signal using at least one of a discrete Fourier transform (DFT) or a fast Fourier transform (FFT).

6. The method of claim 1, wherein the converting of the processed frequency-domain signal to the time-domain comprises:
   converting the processed frequency-domain signal to the time-domains using at least one of an inverse DFT (IDFT) or an inverse FFT (IFFT).

7. A non-transitory computer-readable storage medium comprising stored program instructions configured to cause a processor to perform the method of claim 1.

8. The method of claim 1, wherein the biosignal is a waveform of a sensed physiological movement.

9. The method of claim 1, further comprising:
   receiving the biosignal from an electrocardiogram (ECG), photoplethysmogram (PPG), or electromyogram (EMG) biosignal sensor.

10. The method of claim 1, wherein the performing of the signal processing comprises:
    obtaining a first frequency component from the frequency-domain signal based on a determined number of times a basic waveform of the biosignal repeats during the time interval; and
    removing, from the frequency-domain signal, a second frequency component corresponding to a remainder, excluding the first frequency component, of frequency components of the frequency-domain signal.

11. The method of claim 10, wherein the obtaining of the first frequency component comprises:
    extracting, from the frequency-domain signal, frequency components corresponding to an integer multiple of the number of times the basic waveform of the biosignal repeats during the time interval.

12. The method of claim 10, wherein the first frequency component comprises frequency components corresponding to an integer multiple of an inverse value of the time period.

13. The method of claim 10, wherein the removing of the second frequency component further comprises:
    removing complex conjugates of the second frequency components from the frequency-domain signal.

14. The method of claim 10, wherein the removing of the second frequency component comprises:
    setting the second frequency component to zero.

15. The method of claim 14, wherein the removing of the second frequency component further comprises:
    setting complex conjugates of the second frequency components in the frequency-domain signal to zero.

16. A processor-implemented biosignal processing method, comprising:
    estimating a time period from a biosignal in a time-domain;
    converting, based on the time period, a biosignal corresponding to a time interval of the biosignal to a frequency-domain signal;
    performing signal processing to remove a distortion component from the frequency-domain signal; and
    generating a reconstructed time-domain biosignal, as a reconstruction of the biosignal corresponding to the time interval, by converting a processed frequency-domain signal, obtained through the signal processing, to the time-domain,
    wherein the performing of the signal processing comprises:
    obtaining a first frequency component from the frequency-domain signal based on a determined number of times a basic waveform of the biosignal repeats during the time interval; and
    removing, from the frequency-domain signal, a second frequency component corresponding to a remainder excluding the first frequency component.

17. The method of claim 16, wherein the obtaining of the first frequency component comprises:
    extracting, from the frequency-domain signal, frequency components corresponding to an integer multiple of the number of times the basic waveform of the biosignal repeats during the time interval.

18. The method of claim 16, wherein the first frequency component comprises frequency components corresponding to an integer multiple of an inverse value of the time period.

19. The method of claim 16, wherein the removing of the second frequency component comprises:
    setting, to a conjugate value, second frequency components at symmetrical frequencies in a frequency domain of the frequency-domain signal.

20. The method of claim 16, wherein the removing of the second frequency component comprises:
    setting the second frequency component to zero.

21. A processor-implemented biosignal processing method, comprising:
    receiving a biosignal in a time-domain from an electrocardiogram (ECG), photoplethysmogram (PPG), or electromyogram (EMG) biosignal sensor;
    estimating a time period from the biosignal;
    converting, based on the time period, a biosignal corresponding to a time interval of the biosignal to a frequency-domain signal;

performing signal processing to remove a distortion component from the frequency-domain signal; and generating a reconstructed time-domain biosignal, as a reconstruction of the biosignal corresponding to the time interval, by converting a processed frequency-domain signal, obtained through the signal processing, to the time-domain.

22. An apparatus with biosignal processing, comprising:
a transmitting or receiving interface configured to receive a biosignal; and
a processor configured to
- estimate a time period from the biosignal in a time-domain,
- convert, based on the time period, a biosignal corresponding to a time interval of the biosignal to a frequency-domain signal,
- perform signal processing to remove a determined distortion component from the frequency-domain signal, and
- generate a reconstructed time-domain biosignal, as a reconstruction of the biosignal corresponding to the time interval, through a conversion of a processed frequency-domain signal, obtained through the signal processing, to the time-domain.

23. The apparatus of claim 22, wherein the biosignal comprises a form in which a basic waveform is repeated in the biosignal during the time period.

24. The apparatus of claim 22, wherein, for the performing of the signal processing, the processor is configured to obtain a first frequency component from the frequency-domain signal based on a determined number of times a basic waveform of the biosignal repeats during the time interval, and remove a second frequency component, corresponding to a remainder excluding the first frequency component, from the frequency-domain signal.

25. The apparatus of claim 24, wherein, for the obtaining of the first frequency component, the processor is configured to extract, from the frequency-domain signal, frequency components corresponding to an integer multiple of the number of times the basic waveform of the biosignal repeats during the time interval.

26. The apparatus of claim 24, wherein the first frequency component comprises frequency components corresponding to an integer multiple of an inverse value of the time period.

27. The apparatus of claim 24, wherein, for the removing of the second frequency component, the processor is further configured to remove complex conjugates of the second frequency components from the frequency-domain signal.

28. The apparatus of claim 24, wherein, for the removing of the second frequency component, the processor is configured to set the second frequency component to zero.

29. The apparatus of claim 22, wherein the time interval corresponds to an integer multiple of the time period.

30. The apparatus of claim 22, wherein, for the converting of the biosignal corresponding to the time interval, the processor is configured to extract the biosignal corresponding to the time interval from the biosignal, and convert the extracted biosignal to the frequency-domain signal based on a determined number of times a basic waveform of the biosignal repeats during the time interval.

31. The apparatus of claim 30, wherein, for the converting of the extracted biosignal, the processor is configured to convert the extracted biosignal to the frequency-domain signal using at least one of a discrete Fourier transform (DFT) or a fast Fourier transform (FFT).

32. The apparatus of claim 22, wherein, for the converting of the processed frequency-domain signal to the time interval, the processor is configured to convert the processed frequency-domain signal to the time-domain using at least one of an inverse DFT (IDFT) or an inverse FFT (IFFT).

33. A processor-implemented biosignal processing method, comprising:
- sensing a periodic physiological movement as a biosignal in a time-domain;
- extracting a plurality of periods from the biosignal;
- converting the extracted plurality of periods to a frequency-domain signal;
- isolating, based on a number of the plurality of periods, a reconstruction component from a distortion component of the frequency-domain signal; and
- generating a reconstructed time-domain biosignal, as a reconstruction of the extracted plurality of periods, by converting the reconstruction component to the time-domain.

34. A biosignal processing system, the system comprising:
a sensor configured to sense a periodic physiological movement as a biosignal in a time-domain; and
a processor configured to:
- extract a plurality of periods from the biosignal;
- convert the extracted plurality of periods to a frequency-domain signal;
- isolate, based on a number of the plurality of periods, a reconstruction component from a distortion component of the frequency-domain signal; and
- generate a reconstructed time-domain biosignal, as a reconstruction of the extracted plurality of periods, by converting the reconstruction component to the time-domain.

* * * * *